(12) United States Patent
Yoneda et al.

(10) Patent No.: US 11,617,794 B2
(45) Date of Patent: Apr. 4, 2023

(54) DRUG COMPOSITION AND SOFT CAPSULE DRUG SEALING THE DRUG COMPOSITION

(71) Applicant: TAIKO PHARMACEUTICAL CO., LTD., Suita (JP)

(72) Inventors: Yuji Yoneda, Suita (JP); Kaori Nakagawa, Suita (JP)

(73) Assignee: TAIKO PHARMACEUTICAL CO., LTD., Suita (JP)

( * ) Notice: Subject to any disclaimer, the term of this patent is extended or adjusted under 35 U.S.C. 154(b) by 1006 days.

(21) Appl. No.: 14/387,926

(22) PCT Filed: Mar. 19, 2013

(86) PCT No.: PCT/JP2013/057828
§ 371 (c)(1),
(2) Date: Sep. 25, 2014

(87) PCT Pub. No.: WO2013/146471
PCT Pub. Date: Oct. 3, 2013

(65) Prior Publication Data
US 2015/0057370 A1    Feb. 26, 2015

(30) Foreign Application Priority Data

Mar. 28, 2012 (JP) .............................. JP2012-074394

(51) Int. Cl.
| A61K 47/44 | (2017.01) |
| A61K 9/48 | (2006.01) |
| A61K 47/10 | (2017.01) |
| A61K 47/42 | (2017.01) |
| A61K 47/14 | (2017.01) |

(52) U.S. Cl.
CPC ............ *A61K 47/44* (2013.01); *A61K 9/4825* (2013.01); *A61K 9/4858* (2013.01); *A61K 47/10* (2013.01); *A61K 47/42* (2013.01)

(58) Field of Classification Search
CPC ....... A61K 47/44; A61K 47/10; A61K 9/4825
See application file for complete search history.

(56) References Cited

U.S. PATENT DOCUMENTS

| 4,608,258 | A | * | 8/1986 | Yamanaka | ............. | A61K 31/05 424/725.1 |
| 5,112,872 | A | * | 5/1992 | Baba | ................... | A61K 31/085 514/73 |
| 5,431,916 | A | * | 7/1995 | White | .................. | A61K 9/4858 424/451 |
| 6,730,333 | B1 | | 5/2004 | Garrity et al. | | |
| 2006/0093679 | A1 | * | 5/2006 | Mayer | ................. | A61K 31/192 424/490 |
| 2011/0251167 | A1 | * | 10/2011 | Dudley | ............... | A61K 31/568 514/178 |

FOREIGN PATENT DOCUMENTS

| CA | 2005072 | | * | 12/1994 | | |
| CA | 2 304 493 | A1 | | 4/1999 | | |
| CN | 101152307 | A | | 4/2008 | | |
| DE | 4422938 | A1 | * | 1/1995 | | |
| DE | 4422938 | A1 | * | 1/1995 | ........... | A61K 9/4825 |
| EP | 4422938 | A1 | * | 1/1995 | ............. | A61K 31/44 |
| EP | 0 815 865 | A2 | | 1/1998 | | |
| GB | 1 060 258 | A | | 3/1967 | | |
| JP | 50106877 | A | * | 8/1975 | | |
| JP | 10-310520 | A | | 11/1998 | | |
| JP | 2002-201140 | A | | 7/2002 | | |
| RU | 2336887 | C2 | | 10/2008 | | |

OTHER PUBLICATIONS

Definition of capsule by Merriam-Webster. (Year: 2019).*
Tetraglycol (CAS 31692-85-0) (Year: 2019).*
Polysorbate 80 Identification (obtained online via www.google.com (Year: 2020).*
"Guaiacol" obtained via www.chemicalbook.com, p. 1-6. (Year: 2020).*
European Search Report dated Oct. 16, 2015, by the European Patent Office, in corresponding European Patent Application No. 110967P842PCEP. (9 pages).
Taiwanese Office Action dated Apr. 26, 2016, by the Taiwanese Patent Office in corresponding Taiwanese Patent Application No. 102110719 (6 pages).
Russian Official Action issued Dec. 28, 2016, by the Russian Patent Office, in corresponding Russian Patent Application No. 2014143264 (10 pages) with English-language translation.
Www.risnet.ru_tn_index_id_15226; Composition and form of release, Jul. 18, 2005, with partial translation (4 pages).
International Search Report (PCT/ISA/210) mailed on May 14, 2013, by the Ja as the International Searching Authority for International Application No. PCTI.
Written Opinion (PCT/ISA/237) mailed on May 14, 2013, by the Japanese Pate International Searching Authority for International Application No. PCT/JP2013.
Gorinstein, S et al., A comparative study of phenolic compounds and antic antiproliferative activities in frequently consumed raw vegetables, Eur Food Re (month unknown), vol. 228, No. 6, pp. 903-911.

* cited by examiner

*Primary Examiner* — Mina Haghighatian
(74) *Attorney, Agent, or Firm* — Buchanan Ingersoll & Rooney PC

(57) ABSTRACT

A drug composition in a liquid form sealed within a soft capsule containing succinylated gelatin as a principal component thereof, the composition including (a) one kind of phenol derivative or a mixture of multiple kinds thereof and (b) a succinylated-gelatin insolubilizing agent; and a soft capsule drug including a capsule shell containing succinylated gelatin as a principal component thereof, the shell sealing therein a drug composition in a liquid form including (a) one kind of phenol derivative or a mixture of multiple kinds thereof; and (b) a succinylated-gelatin insolubilizing agent.

8 Claims, No Drawings

DRUG COMPOSITION AND SOFT CAPSULE DRUG SEALING THE DRUG COMPOSITION

TECHNICAL FIELD

The present invention relates to a drug composition and a soft-shelled or soft capsule drug sealing the drug composition ("soft capsule drug"). More particularly, the invention relates to a drug composition in a liquid form that can be stored inside a capsule in a stable manner for a long period of time, without dissolving a shell of the capsule. The invention relates also to a soft-shelled or soft capsule drug sealing the inventive drug composition, which is readily soluble, highly resistant against collapse delay and is superior in storage stability.

BACKGROUND ART

Conventionally, a soft capsule drug commonly used as a medical product or a supplement has employed gelatin or glycerin as the principal component of its shell. However, with the conventional soft capsule drug, there was the possibility of solubility as a capsule drug deteriorating due to insolubilization of the principal component of the capsule shell. With this, there occurs deterioration in the collapsibility of the soft capsule drug, resulting in collapse delay, which in turn affects adversely e.g. bioavailability.

In order to prevent such solubility (shell collapsibility) deterioration of the capsule shell of the capsule drug, there has been proposed to employ, as the principal component of the capsule shell, succinylated gelatin obtained by causing gelatin as the principal component of the capsule shell to react with succinic anhydride which is an organic acid (see Patent Document 1).

PRIOR-ART DOCUMENT

Patent Document

Patent Document 1: Japanese Unexamined Patent Application Publication No. 10-310520

SUMMARY OF INVENTION

Problem to be Solved by Invention

With the technique disclosed in Patent Document 1, it was made possible to provide a soft capsule drug having good solubility as well as high collapse delay resistance. However, when an organic compound (a phenol derivative, etc.) having a hydrophilic group such as a hydroxyl group in its molecule is sealed within a capsule shell, depending on the contents (drug), there would occur a problem of the contents dissolving this capsule shell.

Therefore, the object of the present invention is to provide a drug composition capable of preventing dissolving of the shell by contents (drug) even when an organic compound (a phenol derivative, etc.) having a hydrophilic group such as a hydroxyl group in its molecule is sealed therein and to provide also a soft capsule drug containing such drug composition.

Means for Solving the Problem

After conducting intensive and extensive research and development effort, the present inventors discovered that the above-described problem can be solved by using a succinylated-gelatin insolubilizing agent such as a surface active agent in combination with the organic compound (a phenol derivative or the like) and arrived at the present invention.

A drug composition relating to the present invention for fulfilling the above-noted object is a drug composition in a liquid form sealed within a soft capsule containing succinylated gelatin as a principal component thereof, and a first characterizing feature thereof resides in that the composition comprises: (a) one kind of phenol derivative or a mixture of multiple kinds thereof; and (b) a succinylated-gelatin insolubilizing agent.

With the above-described arrangement, even if one kind of phenol derivative or a mixture of multiple kinds thereof (to be referred to simply as "(a) component" hereinafter) is sealed (filled) within a soft capsule containing succinylated gelatin as a principal component thereof, it is still possible to prevent dissolving of the capsule shell during storage.

According to a second characterizing feature of the drug composition relating to the present invention, said one kind of phenol derivative or mixture of multiple kinds thereof (a) comprises wood creosote or a constituent thereof.

If the contents comprise wood creosote or a constituent thereof as provided in the above arrangement, the advantageous effect of the inventive subject matter of the first characterizing feature (effect of preventing dissolving of capsule shell) will be exhibited conspicuously. And, it becomes possible to encapsulate wood creosote or a constituent thereof which was conventionally believed to be impossible.

According to a third characterizing feature of the drug composition relating to the present invention, said succinylated-gelatin insolubilizing agent (b) comprises a surface active agent.

If the succinylated-gelatin insolubilizing agent (b) comprises a surface active agent as provided in the above-described arrangement, the effect of preventing dissolving of capsule shell will be exhibited even more conspicuously. Incidentally, what is referred to herein as "a surface active agent" is meant to include also a so-called antifoaming agent, an emulsifier, a wetting agent, a cleaning agent and a dispersing agent.

Further, if the succinylated-gelatin insolubilizing agent (b) employed comprises a surface active agent, whose HLB value is 8 or more, the effect of preventing dissolving of capsule shell will be exhibited even more conspicuously.

According to a fourth characterizing feature of the drug composition relating to the present invention, the succinylated-gelatin insolubilizing agent (b) comprises a compound containing a polymer chain having repeats of an oxyethylene group represented by Chemical Formula 1 below,

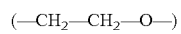 [Chemical Formula 1]

With the above arrangement, the effect of preventing dissolving of capsule shell will be exhibited even more conspicuously.

According to a fifth characterizing feature of the drug composition relating to the present invention, the succinylated-gelatin insolubilizing agent (b) comprises a compound containing a polymer chain having repeats of an oxyethylene group represented by Chemical Formula 1 below by 45 weight % or more,

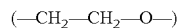 [Chemical Formula 1]

If the repeats of an oxyethylene group (polyoxyethylene polymer chain) is contained by 45 weight % or more (preferably by 60 weight % or more, but below 100 weight %) in the succinylated-gelatin insolubilizing agent (b), the effect of preventing dissolving of capsule shell will be exhibited even more conspicuously.

According to a first characterizing feature of a soft capsule drug relating to the present invention, the soft capsule drug comprises a capsule shell containing succinylated gelatin as a principal component thereof, the shell sealing therein a drug composition in a liquid form comprising (a) one kind of phenol derivative or a mixture of multiple kinds thereof; and (b) a succinylated-gelatin insolubilizing agent.

With the above-described arrangement, it is possible to prevent the contents (a drug composition in a liquid form comprising (a) one kind of phenol derivative or a mixture of multiple kinds thereof) from dissolving the capsule shell. Hence, there can be obtained a soft capsule drug having distinguished storage stability as being capable of storing contents for a long period of time.

According to a second characterizing feature of the soft capsule drug relating to the present invention, said one kind of phenol derivative or mixture of multiple kinds thereof (a) comprises wood creosote or a constituent thereof.

If the contents comprise wood creosote or a constituent thereof as provided in the above arrangement, the advantageous effect of the inventive subject matter of the fourth characterizing feature (effect of preventing dissolving of capsule shell) will be exhibited conspicuously. And, it becomes possible to encapsulate wood creosote or a constituent thereof which was conventionally believed to be impossible.

According to a third characterizing feature of the soft capsule drug relating to the present invention, said succinylated-gelatin insolubilizing agent (b) comprises a surface active agent.

If the succinylated-gelatin insolubilizing agent (b) comprises a surface active agent as provided in the above-described arrangement, the effect of preventing dissolving of capsule shell will be exhibited even more conspicuously. Further, if the succinylated-gelatin insolubilizing agent (b) employed comprises a surface active agent, whose HLB value is 8 or more, the effect of preventing dissolving of capsule shell will be exhibited even more conspicuously.

According to a fourth characterizing feature of the soft capsule drug relating to the present invention, the succinylated-gelatin insolubilizing agent (b) comprises a compound containing a polymer chain having repeats of an oxyethylene group represented by Chemical Formula 1 below,

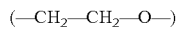  [Chemical Formula 1]

With the above arrangement, the effect of preventing dissolving of capsule shell will be exhibited even more conspicuously.

According to a fifth characterizing feature of the soft capsule drug relating to the present invention, the succinylated-gelatin insolubilizing agent (b) comprises a compound containing a polymer chain having repeats of an oxyethylene group represented by Chemical Formula 1 below by 45 weight % or more,

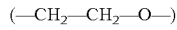  [Chemical Formula 1]

If the repeats of an oxyethylene group (polyoxyethylene polymer chain) is contained by 45 weight % or more (preferably by 60 weight % or more, but below 100 weight %) in the the succinylated-gelatin insolubilizing agent (b), the effect of preventing dissolving of capsule shell will be exhibited even more conspicuously.

Modes of Embodying the Invention

A drug composition according to the present invention is a drug composition in a liquid form sealed within a soft capsule containing succinylated gelatin as a principal component thereof, the composition comprising: (a) one kind of phenol derivative or a mixture of multiple kinds thereof; and (b) a succinylated-gelatin insolubilizing agent.

Succinylated Gelatin

Succinylated gelatin used in the present invention can be obtained by the conventionally known method. That is, succinylated gelatin is a succinyl derivative of gelatin obtained by causing gelatin to be reacted with succinic anhydride in the presence of an alkali. Of the gelatin components in the capsule shell for use in the present invention, the ratio of succinylated gelatin is not particularly limited, but ratio ranges preferably from 60 to 100 weight % (may be referred to simply as "%" when appropriate hereinafter), more preferably from 90 to 100%. As other gelatin components permissible to be contained other than succinylated gelatin, Japanese Pharmacopoeia gelatin, acidic gelatin, alkaline gelatin, organic acid gelatin, peptide gelatin, etc, can be cited.

Phenol Derivative: Component (a)

As examples of phenol derivative (phenolic compound) for use in the present invention, e.g. wood creosote, or its constituents such as guaiacol, creosol, phenol, p-cresol, 4-ethylguaiacol, o-cresol, which are in liquid form at the room temperature, can be cited. These may be used solo or multiple thereof may be used in combination.

Succinylated-Gelatin Insolubilizing Agent:
Component (b)

The succinylated-gelatin insolubilizing agent (b) for use in the present invention is not particularly limited, as long as it is an agent capable of preventing dissolving of the soft capsule shell (succinylated gelatin) by the phenol derivative (component (a)). As some non-limiting examples of succinylated-gelatin insolubilizing agent (b), e.g. a surface active agent (negative ion surface active agent (anion surface active agent), positive ion surface active agent (cation surface active agent), amphoteric surface active agent (zwitterionic surface active agent), non-ionic surface active agent, can be cited.

The surface active agent is meant to be inclusive of a so-called antifoaming agent, an emulsifier, a wetting agent, a cleaning agent and a dispersing agent (note that these names of agent are not necessarily used with clear distinction therebetween in the art at present), As some non-limiting examples of surface active agent, the following agents which are classified as "surface active agent" in "Encyclopedia of Medical Additives" (published by Yakuji Nippo Limited), "Japanese Standard of Food Additives" (published by Hirokawa-Shoten Ltd,) can be cited: PEG's (macrogols) such as polyethylene glycol 200, polyethylene glycol 300, polyethylene glycol 400, phospholipids, glycerin-fatty acid ester, polyglycerin-fatty acid ester, polyethylene glycol fatty acid ester, sorbitan fatty acid ester, polyoxyethylene hydrogenated castor oil, polyoxylated castor oil such as polyoxyl 35 castor oil, polyoxyethylene cetylether, polyoxyethylene stearylether, polyoxyethylene nonylphenyl ether, polyoxyethylene polyoxypropylene glycol, polyoxyethylene sorbitan acid monolaurate, polysorbates, sorbitan monooleate, glyceride monostearate, monooxyethyelene sorbitan monopalminate, monooxyethyelene sorbitan monostearate, polyoxyethylene sorbitan monooleate, sorbitan monostearate, sorbitan monopalmitate, sorbitan monolaurate, sodium lauryl sulfate, polyoxyethylene polyoxypropylene block copolymer, polysorbates such as polysorbate 20, polysorbate 40, polysorbate 60, polysorbate 65, polysorbate 80, macrogols, sucrose fatty acid ester, medium chain triglyceride, tri (caprylic/capric) glyceride, propyleneglycol fatty acid ester (dispersing agent), etc. These may be used solo or two or more kinds of them may be used in combination.

As examples of the succinylated-gelatin insolubilizing agent (b) other than the surface active agents, e.g. a plasticizing agent, a coating agent, can be cited. More specifically, triethyl citrate (a plasticizing agent, a coating agent), (some) propylene glycol fatty acid esters, (some) polyglycerin fatty acid esters, etc. can be cited.

In particular, the succinylated-gelatin insolubilizing agent (b) comprises preferably a compound containing a polymer chain (a compound having a polyoxyethylene chain) having repeats of a structural formula (an oxyethylene group) represented by Chemical Formula 1 below,

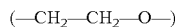  [Chemical Formula 1]

Preferably, the total number of repeats contained in one molecule ranges from 5 to 30, more preferably from 7 to 23, in the respects of readiness of handling, readiness of availability and shell dissolution preventing effect. Incidentally, in case the above compound is a branched compound and the structure represented by Chemical Formula 1 are dispersed on the chain of one molecule, the total number is the number of repeats (polymerization degree).

As some non-limiting examples of the above compound, polysorbates such as polysorbate 20, polysorbate 40, polysorbate 60, polysorbate 65, polysorbate 80, PEG's macrogols such as polyethylene glycol 200, polyethylene glycol 300, polyethylene glycol 400, and polyoxylated castor oil such as polyoxyl 35 castor oil, can be cited. As some preferred examples, Polysorbate 80 (sorbitan polyoxyethylene oleate, Tween® 80, average molecular weight: about 1300, HLB 15, containing about 67 weight % of polyoxyethylene chain), polyethylene glycol 400 (macrogol 400, average molecular weight about 400, containing about 99 weight % of polyoxyethylene chain) or polysorbate 80 in combination with polyethylene glycol 400 (use of mixture) are most preferred, due to conspicuous effect of capsule shell dissolution prevention (reduction).

As the succinylated-gelatin insolubilizing agent (b), two or more kinds thereof may be used in combination as described above. In such case, for the purpose of preventing (reduction) dissolution of the capsule drug skin, it is preferred that always at least one of polysorbate 80 and polyethylene glycol 400 be contained therein. As preferred mixing ratios, at least one of polysorbate 80 and polyethylene glycol 400 is contained by 30 weight % or more, preferably by 50 weight % or more, still preferably by 60 weight % or mere.

The amount of the succinylated-gelatin insolubilizing agent (b) to be used is not particularly limited. However, preferably, for one part (1 weight part) of one kind of phenol derivative or mixture of multiple kinds thereof (component (a)(e.g. wood creosote), the component (b) should be contained by from 0.3 to 10 times in amount. If the amount is below 0.3 times, there will arise the possibility of obtaining the skin dissolution preventing effect by the component (a) becoming difficult. On the other hand, if an amount greater than 10 times is used, there is the possibility the capsule skin dissolution preventing effect not improving significantly, thus inviting cost disadvantage. And, there will also tend to invite a problem of the particle or grain size of the soft capsule drug as a final product becoming large. More preferred range of the succinylated-gelatin insolubilizing agent (b) to be used is from 0.5 times (same quantity) to 8 times, more preferably from 0.8 times to 6 times in amount, relative to 1 part of the component (a).

Preferably, the average molecular weight (to be referred to simply as "molecular weight" hereinafter) of the succinylated-gelatin insolubilizing agent (b) should be 300 or more, more preferably from 400 to 2000, still more preferably from 500 to 1500. If the molecular weight is smaller than 400, it becomes difficult to obtain the effect of preventing (decreasing) the dissolution of capsule skin. On the other hand, if the molecular weight is greater than 1500, this will result in increase of the viscosity of the drug composition, which in turn can make a charging (sealing) operation thereof into the soft capsule shell difficult.

Further, in case the succinylated-gelatin insolubilizing agent (b) is a surface active agent, it is preferred that this agent has an HLB (Hydrophilic-Lipophilic-Balance) value of 8 or more as such arrangement will prevent (reduce) shell dissolution even more effectively, more preferably from 8 to 18, still more preferably from 10-16.

Incidentally, HLB is a numeric value obtained by multiplying the weight fraction of the hydrophilic group by 20 according to the Griffin's definition. If HLB is smaller than 8, this will make it difficult to obtain the effect of preventing (reducing) capsule shell dissolution.

The drug composition containing a phenol derivative (component (a)) and a succinylated-gelatin insolubilizing agent (component (b)) can be transparent and clear (in the form of transparent/semi-transparent liquid) or can be a turbid (non-transparent) suspended liquid matter rendered turbid by addition of a herbal medicine as a third component. However, it is preferred that the composition be a clear liquid substance as it will give aesthetic value and enhanced commercial value as a final product (soft capsule drug) to consumers.

Other Components

In addition to the above, as components (additives) that can be mixed in the inventive drug composition or the capsule shell (base material), a light shielding agent, a plasticizing agent, a coloring agent, etc. can be cited.

As some examples of the light shielding agent, a component for inhibiting absorption of light such as ultraviolet beam, a component serving as a coloring agent, can be cited. More specifically, titanium oxide, yellow ferric oxide, Food Yellow No. 4 (Tartrazine), Food Yellow No. 5, Food Red No. 3, Food Red No. 102, Food Red No. 105, Food Red No. 106, etc. can be cited. These may be used solo or multiple of them may be used in combination.

As some non-limiting examples of the plasticizing agent, concentrated glycerin, D-sorbitol, etc. can be cited.

Capsule Shell

By reducing the contents of concentrated glycerin and/or water in the capsule shell containing succinylated gelatin as the principal component, it is possible to reduce leak of odor (or smell) of the contents (drug) to be sealed (filled) in the capsule. That is, by setting the content of concentrated glycerin in the capsule shell to 7% or lower, preferably to 6% to 4% and/or reducing the water content to 9 to 6%, it is possible to reduce leak of odor or smell of the contents (drug) to be sealed (filled) in the capsule. This arrangement can be an effective measure for preventing leak of odor or smell of the contents to be sealed or filled in the capsule to the outside of the capsule, in case the contents (drug) have a strong smell such as wood creosote or a constituent thereof such as guaiacol, creosol, phenol, p-cresol, 4-ethylguaiacol, o-cresol.

Other Matters

The dose in case the contents ((a) component) in the soft capsule drug is wood creosote or a constituent thereof will be selected appropriately, depending on the sex, age, body weight, the condition of the patient, etc. In general, however, for an adult, the above-described effective component can be administered by 1 to 500 mg approximately per body kilogram per day, preferably by 2 to 100 mg approximately, more preferably by 2 to 25 mg approximately. And, these may be administered in separate portions in 2 to 4 times per day.

EXAMPLES

Next, one embodiment of the present invention will be explained. It should be noted however that the present invention is not limited thereto.

Formulation Examples 1-2 (Soft Capsule Shell Formulations)

The respective components shown in Table 1 below were mixed by the ratios (weight parts, may be referred to simply as "parts" hereinafter) indicated therein and soft capsule raw sheets were made by the conventional method (Formulation Examples 1, 2-1, 2-2).

TABLE 1

|  |  | formulation example 1 | formulation example 2-1 | formulation example 2-2 |
|---|---|---|---|---|
| capsule drug shell | succinylated gelatin | 100 parts | 100 parts | 100 parts |
|  | concentrated glycerin | 20 parts | 20 parts | 20 parts |

TABLE 1-continued

|  |  | formulation example 1 | formulation example 2-1 | formulation example 2-2 |
|---|---|---|---|---|
| mixing ratio | D-sorbitol solution | 20 parts | 20 parts | 20 parts |
|  | caramel | 0.3 parts | 0.3 parts | 0.3 parts |
|  | crystalline cellulose | 0 parts | 0 parts | 10 parts |
|  | purified water | 105 parts | 105 parts | 95 parts |
| drug shell water content (%) |  | 8.6 | 8.5 | 8.7 |

Examples 1-3, Comparison Example 1 (Formulation of Drug Composition, Manufacture of Soft Capsule Drug)

The respective components shown in Table 2 below were mixed by ratios indicated therein and clear drug compositions containing wood creosote and a succinylated-gelatin insolubilizing agent such as a surface active agent were prepared. And, with using the soft capsule raw sheets obtained as described above, soft capsule drugs (soft capsules) encapsulating the drug composition were made by the standard method. It is noted that the drug shell water contents (%) shown in Table 1 above are water contents of the capsule drug shells (matrices) of the soft capsule drugs as measured at this timing (at the timing of completion of charging and drying process).

TABLE 2

|  |  |  | Example 1 | Example 2 | Example 3 | Comparison Example 1 |
|---|---|---|---|---|---|---|
|  | employed soft capsule raw sheet |  | formulation example 1 | formulation example 2-1 | formulation example 2-2 | formulation example 2-1 |
| formulation of drug composition | wood creosote | HLB value | 45 parts | 45 parts | 45 parts | 45 parts |
|  | Polysorbate 80 | 15 | 35 parts | 35 parts | 35 parts |  |
|  | polyoxyl 35 castor oil | 12~14 | 20 parts |  |  |  |
|  | glycerin fatty acid ester (*1) | 10.3 |  | 20 parts | 20 parts |  |
|  | sesame oil |  |  |  |  | 55 parts |

*1 tetraglycerin monolaurate (SY-Glyster ML-310, manufactured by Sakamoto Yakuhin Kogyo Co., Ltd. HLB10.3)

The respective soft capsule drugs obtained as above were subjected to stability test (50° C., 30 days). The results are shown in Table 3 below.

TABLE 3

|  | Example 1 | Example 2 | Example 3 | Comparison Example 1 |
|---|---|---|---|---|
| results of stability test (50° C., 30 days) | No dissolution of capsule drug shell observed | No dissolution of capsule drug shell observed | No dissolution of capsule drug shell observed | Dissolution of capsule drug shell confirmed |

As may be understood from Table 3 above, in a soft capsule drug sealing (charged with) wood creosote, the contents did not dissolve the capsule drug shell only when a succinylated-gelatin insolubilizing agent such as a surface active agent was employed in combination.

Formulation Examples 3-4 (Formulation of Soft Capsule Drug)

The respective components shown in Table 4 below were mixed by ratios indicated therein and soft capsule raw sheets were made by the conventional method (Formulation Examples 3-1~3-3, 4-1~4-3).

TABLE 4

|  |  | formulation example 3-1 | formulation example 3-2 | formulation example 3-3 | formulation example 4-1 | formulation example 4-2 | formulation example 4-3 |
|---|---|---|---|---|---|---|---|
| capsule drug shell mixing ratio | succinylated gelatin | 100 parts | 100 parts | 100 parts | 100 parts | 100 parts | 100 parts |
|  | concentrated glycerin | 10 parts | 10 parts | 10 parts | 15 parts | 15 parts | 15 parts |
|  | D-sorbitol solution | 20 parts | 20 parts | 20 parts | 20 parts | 20 parts | 20 parts |
|  | caramel | 0.3 parts | 0.3 parts | 0.3 parts | 0.3 parts | 0.3 parts | 0.3 parts |
|  | purified water | 105 parts | 105 parts | 105 parts | 105 parts | 105 parts | 105 parts |
| drug shell water content (%) |  | 6% | 7% | 8% | 6% | 7% | 8% |

Examples 4-9 (Formulation of Drug Composition, Manufacture of Soft Capsule Drug)

With using the soft capsule raw sheets obtained as described above, soft capsule drugs (soft capsules) were made by the standard method. The drug compositions sealed (charged) in these soft capsule drugs are as shown in Table 5 below. It is noted that the drug shell water contents (%) shown in Table 4 above are water contents of the manufactured soft capsule drug shells (measured at this timing). The water content is adjustable by lengthening or shortening the drying process during the formulation. And, if it is desired to obtain a drug shell having water content of 8% for example, a standard drying process should be effected for about 48 hours. If it is desired to obtain a drug shell having water content of 6% for example, a standard drying process should be effected for about 100 hours.

The respective soft capsule drugs obtained as above were subjected to stability test (50° C., 30 days). The results are shown also in Table 5 below.

TABLE 6

|  | storage period at 40° C. | |
|---|---|---|
|  | 0 month (control) | after 6 months |
| guaiacol amount (control ratio) | 100 | 101.7 |
| guaiacol content | 28.7% | 29.2% |
| collapse test (min.) | 5-7 | 6-7 |

※ guaiacol content in the used wood creosote: 29.4%

From Table 6 above, it was found that the inventive soft capsule has high solubility and high resistance against collapse delay.

Other Examples 10-38 (Dissolution Preventing Effect Tests)

In order to check the shell dissolution preventing effects when using different ratios of the succinylated-gelatin insolubilizing agent such as a surface active agent or using

TABLE 5

|  |  | Example 4 | Example 5 | Example 6 | Example 7 | Example 8 | Example 9 |
|---|---|---|---|---|---|---|---|
| employed soft capsule raw sheet |  | formulation example 3-1 | formulation example 3-2 | formulation example 3-3 | formulation example 4-1 | formulation example 4-2 | formulation example 4-3 |
| formulation of drug composition | wood creosote | 45 parts | 45 parts | 45 parts | 45 parts | 45 parts | 45 parts |
|  | Polysorbate 80 | 30 parts | 30 parts | 30 parts | 30 parts | 30 parts | 30 parts |
|  | polyoxyl 35 castor oil | 25 parts | 25 parts | 25 parts | 25 parts | 25 parts | 25 parts |
| results of stability test (40° C., 6 months) |  | No dissolution of capsule drug shell | No dissolution of capsule drug shell | No dissolution of capsule drug shell | No dissolution of capsule drug shell | No dissolution of capsule drug shell | No dissolution of capsule drug shell |

|  | HLB value |
|---|---|
| Polysorbate 80 | 15 |
| polyoxyl 35 castor oil | 12~14 |

Collapsibility Test after Storage

Separately, with using the wood creosote soft capsule drug (Example 7), stability and collapsibility after storage at 40° C. (6 months storage period in sealed glass bottle) were checked. The results are shown in Table 6 below.

other substances, dissolution preventing effect tests using components shown in the tables below were conducted. As the soft capsule raw sheet, the one obtained in Formulation Example 3-1 was employed. That is, the soft capsule raw sheet obtained in Formulation Example 3-1 was placed within the glass bottle and mixtures of wood creosote and various kinds of succinylated-gelatin insolubilizing agent (drug compositions in liquid form) were collected in a screw tube. Then, in these mixtures (drug compositions), the soft capsule raw sheet in the glass bottle was submerged and then sealed and stored under the condition of 40° C. After storage for two weeks, changes if any in the soft capsule raw sheets were checked with eyes. The molecular weights and HLB values of the used succinylated-gelatin insolubilizing agents are shown in Table 7 below and the results are shown in Tables 8-12 below (○ indicates no change; Δ indicates slight dissolution of the sheet, but not problematic; and X indicates dissolution).

TABLE 7

| list of surface active agent used (general name/commercial name) | | HLB value |
|---|---|---|
| Polysorbate 80 | | 15 |
| polyoxyl 35 castor oil | Cremophor EL | 12~14 |
| triethyl citrate | Citroflex | plasticizing agent, coating agent |
| propylene glycol fatty acid ester | Miglyol 840 | |
| medium chain fatty acid triglyceride | Panasate 810 | 7~9 |
| medium chain fatty acid triglyceride | Panasate 810S | 7~9 |
| tri (caprylic/capric) glyceride | Myritol 325 | molecular weight 465 |
| glycerin-fatty acid ester | SY Glyster ML-310 | 10.3 |
| glycerin-fatty acid ester | SY Glyster MO-5S | 11.6 |
| diglycerin monolaurate | Sunsoft Q-12D | 8.5 |
| decaglyceryl laurate/decaglyerin monolaurate | Sunsoft Q-12S | 15.5 |
| decaglycerin monomyristate | Sunsoft Q-14S | 14.5 |
| decaglycerin monooleate | Sunsoft Q-17S | 12.0 |
| pentaglycerin monolaurate | Sunsoft A-121E | 10.9 |
| pentaglycerin monomyristate | Sunsoft A-141E | 12.2 |
| pentaglycerin monomyristate | Sunsoft A-171E | 13.0 |
| polyglycerin-fatty acid ester | NIKKOL Hexaglyn1-M | 11.0 |
| polyglycerin-fatty acid ester | NIKKOL Decaglyn1-LN | 12.0 |
| polyglycerin-fatty acid ester | NIKKOL ODM-100 | ※1 |

※1: No HLB value as being not surface active agent.
Required HLB value at time of O/W emulsification is 11-13.

TABLE 8

| | Ex. 10 | Ex. 11 | Ex. 12 |
|---|---|---|---|
| | \multicolumn{3}{c}{for 1 part of wood creosote ratio} | | |
| | two times | three times | four times |
| Polysorbate 80 | Δ | Δ | ○ |
| Cremophor EL | Δ | Δ | ○ |

TABLE 9

| | Ex. 13 | Ex. 14 | Ex. 15 | Ex. 16 | Ex. 17 |
|---|---|---|---|---|---|
| wood creosote | 45 | 45 | 45 | 45 | 45 |
| Polysorbate 80 | 100 | | | | |
| Cremophor EL | | 50 | 100 | 150 | 200 |
| triethyl citrate | 50 | 50 | 50 | 50 | 50 |
| total | 195 | 145 | 195 | 245 | 295 |
| result | ○ | Δ | ○ | ○ | ○ |

TABLE 10

| formulation | Ex. 18 | Ex. 19 | Ex. 20 | Ex. 21 | Ex. 22 |
|---|---|---|---|---|---|
| wood creosote | 45 | 45 | 45 | 45 | 45 |
| Polysorbate 80 | 50 | 50 | 50 | 50 | 50 |
| Cremophor EL | 25 | 25 | 25 | 25 | 25 |
| triethyl citrate | 30 | | | | |
| Miglyol 840 | | 30 | | | |
| Panasate 810 | | | 30 | | |
| Panasate 810S | | | | 30 | |
| Myritol 325 | | | | | 30 |
| total | 150 | 150 | 150 | 150 | 150 |
| result | ○ | ○ | ○ | ○ | ○ |

TABLE 11

| formulation | Ex. 23 | Ex. 24 | Ex. 25 | Ex. 26 | Ex. 27 | Ex. 28 | Ex. 29 | Ex. 30 | Ex. 31 | Ex. 32 | Ex. 33 |
|---|---|---|---|---|---|---|---|---|---|---|---|
| wood creosote | 45 | 45 | 45 | 45 | 45 | 45 | 45 | 45 | 45 | 45 | 45 |
| Polysorbate 80 | 20 | 20 | 20 | 20 | 20 | 20 | 20 | 20 | 20 | 20 | 20 |
| SY Glyster ML-310 | 20 | | | | | | | | | | |
| SY Glyster MO-5S | | 20 | | | | | | | | | |
| Sunsoft Q-12D | | | 20 | | | | | | | | |
| Sunsoft Q-12S | | | | 20 | | | | | | | |
| Sunsoft Q-14S | | | | | 20 | | | | | | |
| Sunsoft Q-17S | | | | | | 20 | | | | | |
| Sunsoft A-121E | | | | | | | 20 | | | | |
| Sunsoft A-141E | | | | | | | | 20 | | | |
| Sunsoft A-171E | | | | | | | | | 20 | | |
| NIKKOL Hexaglyn1-M | | | | | | | | | | 20 | |
| NIKKOL Decaglyn1-LN | | | | | | | | | | | 20 |
| total | 85 | 85 | 85 | 85 | 85 | 85 | 85 | 85 | 85 | 85 | 85 |
| result | ○ | ○ | ○ | ○ | ○ | ○ | ○ | ○ | ○ | ○ | ○ |

TABLE 12

| | Ex. 34 | Ex. 35 | Ex. 36 | Ex. 37 | Ex. 38 |
|---|---|---|---|---|---|
| | | for 1 part of wood creosote | | | |
| | 1 time | 2 times | 3 times | 4 times | 5 times |
| SY Glyster ML-310 | Δ | ○ | ○ | ○ | ○ |
| SY Glyster MO-5S | not used | ○ | ○ | ○ | ○ |
| Sunsoft Q-12D | not used | ○ | ○ | ○ | ○ |
| Sunsoft Q-12S | Δ | ○ | ○ | ○ | ○ |
| Sunsoft Q-14S | not used | ○ | ○ | ○ | ○ |
| Sunsoft Q-17S | not used | ○ | ○ | ○ | ○ |
| Sunsoft A-121E | ○ | ○ | ○ | ○ | ○ |
| Sunsoft A-141E | ○ | ○ | ○ | ○ | ○ |
| Sunsoft A-171E | not used | ○ | ○ | ○ | ○ |
| NIKKOL Hexaglyn1-M | not used | ○ | ○ | ○ | ○ |
| NIKKOL Decaglyn1-LN | not used | ○ | ○ | ○ | ○ |

Examples 39-40 (Formulation of Drug Composition, Manufacture of Soft Capsule Drug)

With using the soft capsule raw sheets obtained in formulation example 4-2 above, soft capsule drugs (soft capsules) were made by the standard method. The drug compositions sealed (charged) in these soft capsule drugs are as shown in Table 13 below. It is noted that the drug shell water contents (%) of the used soft capsule raw sheets (obtained in formulation example 4-2) are water contents of the manufactured capsule drug shells (measured at this timing). The respective soft capsule drugs obtained as above were subjected to stability test (50° C., 30 days). The results are shown also in Table 13 below.

TABLE 13

| employed soft capsule raw sheet | | Ex. 39 formulation example 4-2 | Ex. 40 formulation example 4-2 |
|---|---|---|---|
| formulation of drug composition | wood creosote | 45 parts | 45 parts |
| | Polysorhate 80 | 25 parts | 0 parts |
| | Polyethylene glycol 400 | 30 parts | 55 parts |
| results of stability test (50° C., 30 days) | | No dissolution of capsule drug shell observed | No dissolution of capsule drug shell observed |

Collapsibility Test after Storage

Separately, with using the wood creosote soft capsule drugs (Examples 39 and 40), stability and collapsibility after storage at 40° C. (6 months storage period in sealed glass bottle) were checked. The results are shown in Table 14 below

TABLE 14

| | storage period at 40° C. | |
|---|---|---|
| | 0 month (control) | after 6 months |
| guaiacol amount (control ratio) | 100 | 101.7 |
| guaiacol content | 28.7% | 29.2% |
| collapse test (min.) | about 6 min. | about 6 min. |

※ guaiacol content in the used wood creosote: 29.4%

From Table 14 above, it was found that the inventive soft capsule has high solubility and high resistance against collapse delay.

INDUSTRIAL APPLICABILITY

The drug composition of the present invention is applicable as a drug composition in a liquid (solution) form that is stored inside a soft capsule whose capsule shell contains a succinylated-gelatin as a principal component thereof and also as a soft capsule drug sealed in a soft capsule whose capsule shell contains a succinylated-gelatin as a principal component thereof.

The invention claimed is:

1. A drug composition in a liquid form sealed within a soft capsule shell containing succinylated gelatin as a principal component thereof, the shell having a water content of 6 to 9% by weight, the composition comprising:
    (a) wood creosote, wherein the wood creosote is in liquid form at room temperature; and
    (b) a succinylated-gelatin insolubilizing agent;
    the succinylated-gelatin insolubilizing agent is selected from the group consisting of polyethylene glycol 200, polyethylene glycol 300, polyethylene glycol 400, glycerin-fatty acid ester, polyglycerin-fatty acid ester, polyethylene glycol fatty acid ester, sorbitan fatty acid ester, polyoxyethylene hydrogenated castor oil, polyoxylated castor oil, polyoxyethylene cetylether, polyoxyethylene stearylether, polyoxyethylene nonylphenyl ether, polyoxyethylene polyoxypropylene glycol, polyoxyethylene sorbitan acid monolaurate, a polysorbate, sorbitan monooleate, glyceride monostearate, monooxyethyelene sorbitan monopalminate, monooxyethyelene sorbitan monostearate, polyoxyethylene sorbitan monooleate, sorbitan monostearate, sorbitan monopalmitate, sorbitan monolaurate, polyoxyethylene polyoxypropylene block copolymer, a macrogol, sucrose fatty acid ester, medium chain triglyceride, tri (caprylic/capric) glyceride, propyleneglycol fatty acid ester, and a combination thereof,
    wherein the succinylated-gelatin insolubilizing agent (b) is present in an amount of 0.3 to 10 parts by weight, per one part by weight of the wood creosote,
    wherein the wood creosote is the only drug ingredient that is contained in the drug composition.

2. A soft capsule drug comprising a soft capsule shell containing succinylated gelatin, the shell having a water content of 6 to 9% by weight and the shell sealing therein a drug composition in a liquid form comprising:
    (a) wood creosote or a constituent of the wood creosote, wherein the wood creosote or constituent of the wood creosote is in liquid form at room temperature; and
    (b) a succinylated-gelatin insolubilizing agent;
    the succinylated-gelatin insolubilizing agent is selected from the group consisting of polyethylene glycol 200, polyethylene glycol 300, polyethylene glycol 400, glycerin-fatty acid ester, polyglycerin-fatty acid ester, polyethylene glycol fatty acid ester, sorbitan fatty acid ester, polyoxyethylene hydrogenated castor oil, polyoxylated castor oil, polyoxyethylene cetylether, polyoxyethylene stearylether, polyoxyethylene nonylphenyl ether, polyoxyethylene polyoxypropylene glycol, polyoxyethylene sorbitan acid monolaurate, a polysorbate, sorbitan monooleate, glyceride monostearate, monooxyethyelene sorbitan monopalminate, monooxyethyelene sorbitan monostearate, polyoxyethylene sorbitan monooleate, sorbitan monostearate, sorbitan monopalmitate, sorbitan monolaurate, polyoxyethylene polyoxypropylene block copolymer, a macrogol, sucrose fatty acid ester, medium chain triglyceride, tri (caprylic/capric) glyceride, propyleneglycol fatty acid ester, and a combination thereof, wherein the succinylated-gelatin insolubilizing agent (b) is present in an amount of 0.3 to 10 parts by weight, per one part by weight of the wood creosote or a constituent of the wood creosote, wherein the wood creosote or constituent of the wood creosote is the only drug ingredient that is contained in the drug composition.

3. The drug composition according to claim 1, wherein a content of repeats of an oxyethylene group represented by Chemical Formula 1 below in the succinylated-gelatin insolubilizing agent (b) is 45 weight % or more relative to the total weight of the succinylated-gelatin insolubilizing agent (b), $$(-CH_2-CH_2-O-).$$ [Chemical Formula 1]

4. The soft capsule drug according to claim 2, wherein a content of repeats of an oxyethylene group represented by Chemical Formula 1 below in the succinylated-gelatin insolubilizing agent (b) is 45 weight % or more relative to the total weight of the succinylated-gelatin insolubilizing agent (b), $$(-CH_2-CH_2-O-).$$ [Chemical Formula 1]

5. The soft capsule drug according to claim 2, wherein the constituent of the wood creosote comprises guaiacol, cresol, phenol, p-cresol, 4-ethylguaiacol, o-cresol, or a combination thereof.

6. The soft capsule drug according to claim 2, wherein the capsule shell further comprises glycerin.

7. The drug composition according to claim 1, wherein the polysorbate is selected from the group consisting of polysorbate 20, polysorbate 40, polysorbate 60, polysorbate 65, polysorbate 80, and a combination thereof.

8. The soft capsule drug according to claim 2, wherein the polysorbate is selected from the group consisting of polysorbate 20, polysorbate 40, polysorbate 60, polysorbate 65, polysorbate 80, and a combination thereof.

* * * * *